United States Patent [19]
Christy

[11] 3,988,454
[45] Oct. 26, 1976

[54] PHENYLALKYLARALKYLAMINES FOR PHARMACEUTICAL USE

[75] Inventor: Marcia Elizabeth Christy, Perkasie, Pa.

[73] Assignee: Merck & Co., Inc., Rahway, N.J.

[22] Filed: Jan. 3, 1975

[21] Appl. No.: 538,498

Related U.S. Application Data

[60] Division of Ser. No. 428,643, Dec. 27, 1973, Pat. No. 3,896,237, which is a continuation-in-part of Ser. No. 106,889, Jan. 15, 1971, abandoned.

[52] U.S. Cl. .............................. 424/248; 424/246
[51] Int. Cl.$^2$ ................. A61K 31/535; A61K 31/54
[58] Field of Search ........................... 424/246, 428

[56] References Cited
UNITED STATES PATENTS

| | | |
|---|---|---|
| 3,777,026 | 12/1973 | Anderson ........................ 424/248 |
| 3,790,569 | 2/1974 | Mauvernay ....................... 424/248 |
| 3,812,177 | 5/1974 | Engelhardt et al. ................ 424/248 |

*Primary Examiner*—Sam Rosen
*Attorney, Agent, or Firm*—Daniel T. Szura; Harry E. Westlake

[57] ABSTRACT

This application discloses methods of preparing phenylalkylaralkylamines by the lithium aluminum hydride reduction of the corresponding phenylalkylaralkyl nitriles and/or amides. The produced alkylamines are converted to the corresponding N-alkyl and N,N-dialkyl derivatives thereof. The amines and their alkylated derivatives are useful as antiarrhythmics.

2 Claims, No Drawings

PHENYLALKYLARALKYLAMINES FOR PHARMACEUTICAL USE

This is a division of copending application Ser. No. 428,643 filed Dec. 27, 1973 now U.S. Pat. No. 3,896,237 which in turn is a continuation-in-part of application Ser. No. 106,889 filed Jan. 15, 1971, now abandoned.

This invention relates to derivatives of aralkylamine compounds. More specifically, it relates to substituted and unsubstituted derivatives of phenethylbenzylamines, phenethylphenethylamines, and the corresponding N-substituted derivatives such as the N-alkyl and the N,N-dialkyl derivatives thereof.

This invention also relates to methods of treating or preventing cardiac arrhythmias using the novel compounds and/or pharmaceutical formulations thereof, described hereinafter.

The new compounds of my invention are 1,2-diaryl derivatives of ethane wherein one of the aryl substituents is an aromatic ring having at least one of its hydrogens replaced by a straight or branched chain aminoalkyl radical, or an amino heterocyclic radical and in which the other substituent is a homocyclic or heterocyclic ring selected from aryl, substituted aryl, heterocyclic and substituted heterocyclic substituents. The compounds of my invention are represented structurally as follows:

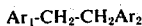

in which $Ar_1$ is a substituted or unsubstituted phenylalkylamine substituent and $Ar_2$ is a substituted or unsubstituted aryl aromatic ring.

A preferred class of compounds of my invention are represented structurally as aralkylamines of the formula:

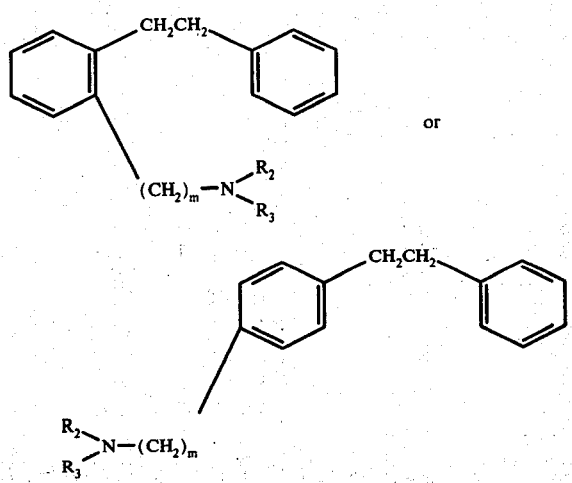

in which $m$ is an integer varying from 1–4 inclusive; and $R_2$ and $R_3$ are either similar or dissimilar and are either hydrogen, alkyl (preferably of from 1–6 carbon atoms), branched chain alkyl, alkenyl, alkynyl (each preferably containing 1–6 carbon atoms), and can be joined together or alternatively may be linked through an atom of carbon, nitrogen, oxygen, or sulfur to one of the methylene substituents bridging the aromatic ring and the amine radical to form a heterocyclic ring of from 5–6 carbon atoms such as 1-piperidyl, 1-pyrrolidinyl, 1-morpholinyl, 4-thiomorpholinyl, or 1-loweralkyl-4-piperazinyl, especially phenyl or substituted phenyl, heterocyclic aromatic or a partially or completely reduced derivative thereof.

A preferred group of such compounds includes derivatives in which one or more of the hydrogens of either or both of the phenyl rings is replaced by substituents selected from the group consisting of an alkyl group having up to 6 carbon atoms, an alkenyl group having up to 6 carbon atoms, a perfluoroalkyl group having up to 4 carbon atoms, a phenyl or a substituted phenyl radical, an acyl group having up to 4 carbon atoms, a perfluoroacyl group having up to 4 carbon atoms, amino, an alkylamino group having up to 4 carbon atoms, a dialkylamino group having up to 8 carbon atoms, an acylamino group having up to 4 carbon atoms, a perfluoroacylamino group having up to 4 carbon atoms, an alkylsulfonylamino group having up to 4 carbon atoms, halogen (fluorine, chlorine, bromine, or iodine), hydroxyl, an alkoxyl group having up to 4 carbon atoms, a perfluoroalkoxyl group having up to 4 carbon atoms, cyano, carboxy, carbamoyl, an alkylcarbamoyl group having up to 5 carbon atoms, a dialkylcarbamoyl group having up to 9 carbon atoms, a carbalkoxy group having up to 6 carbon atoms, mercapto, an alkylmercapto group having up to 4 carbon atoms, a perfluoroalkylmercapto group having up to 4 carbon atoms, an alkylsulfonyl group having up to 4 carbon atoms, a perfluoroalkylsulfonyl group having up to 4 carbon atoms, sulfamoyl, an alkylsulfamoyl group having up to 4 carbon atoms, or a dialkylsulfamoyl group having up to 8 carbon atoms. More than one of these substituents may be on each ring. These substituents are identified in the formula as X or X'.

An especially preferred group of compounds included within the scope of my invention is represented by the formula:

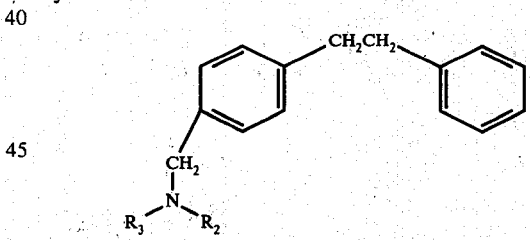

in which $R_2$ and $R_3$ are either hydrogen, alkyl (preferably of from 1–6 carbon atoms), alkenyl, alkynyl (each preferably of from 1–6 carbon atoms), and can be joined together through an atom of carbon, nitrogen, oxygen or sulfur to form a heterocyclic ring of from 5–6 atoms (such as -piperidyl, 1-pyrrolidinyl, 4-morpholinyl, 4-thiomorpholinyl or 1-loweralkyl-4-piperazinyl).

Illustrative of the compounds included within the scope of the invention are 2-(4-bromophenethyl)-benzylamine, 2-(4-bromophenethyl)-phenethylamine, 2-phenethylbenzylamine, 2-phenethyl-phenethylamine, the corresponding N-loweralkyl and the N,N-diloweralkyl derivatives thereof in which the alkyl substituents are either the same or different. Typical of such derivatives are the N-methyl, N-ethyl, N-propyl, N-butyl, N,N-dimethyl, N,N-diethyl, N,N-dipropyl, the N-methyl-N-ethyl, N-ethyl-N-propyl and the N-methyl-N-propyl derivatives thereof.

The compounds represented above, in either their free base or salt form, possess useful pharmacological properties. In particular, they have been found to possess antiarrhythmic activity. It has been found that the administration of compounds of the present invention, depicted in the above formula, results in the prevention of arrhythmia in animals under conditions which ordinarily cause the development of arrhythmia in the animal 100% of the time.

It has further been found that administration of the compounds of the present invention will arrest an existing arrhythmia in the animal being treated and cause a resumption of normal cardiac rhythm. As antiarrhythmic agents, these compounds may be administered orally or parenterally. The formulations for administration may be prepared in conventional manner, employing conventional pharmaceutical carriers and excipients.

The non-toxic acid addition salts useful as components in the compositions provided by the present invention are salts formed by the reaction of an equivalent amount of the amine compound of the above formula and an acid which is pharmacologically acceptable in the intended doses. Salts of the above compound which are useful are salts of the amine with hydrochloric acid, hydrobromic acid, sulfuric acid, phosphoric acid, fumaric acid, acetic acid, propionic acid, lactic acid, gluconic acid, maleic acid, succinic acid, tartaric acid, and the like. Salts of these acids with the amine base are useful as the active component of the compositions in the method of this invention.

The daily doses are based on the total body weight of the test animal and vary between about 1.00 and 100.00 mg./kg. for mature animals. Thus, a unit dose based on four-times-a-day administration is between 2.5 mg. and 250 mg. for a 10 kg. dog, and a total daily dose for a 10 kg. dog would vary between about 10 mg. and 1000 mg. For larger animals, up to 100 kg. and above, proportional dosages are employed, based on the weight of the animal. Suitable dosage units provided for the administration of the compositions used in the method of the invention are tablets, capsules (which may be suitably formulated for either immediate or sustained release), syrups, elixirs, parenteral solutions, and the like. These dosage forms preferably contain per unit one or more multiples of the desired dosage unit in combination with the pharmaceutically acceptable diluent or carrier required for preparing the dosage unit.

The compounds represented by the above structural formulae may be prepared as illustrated below:

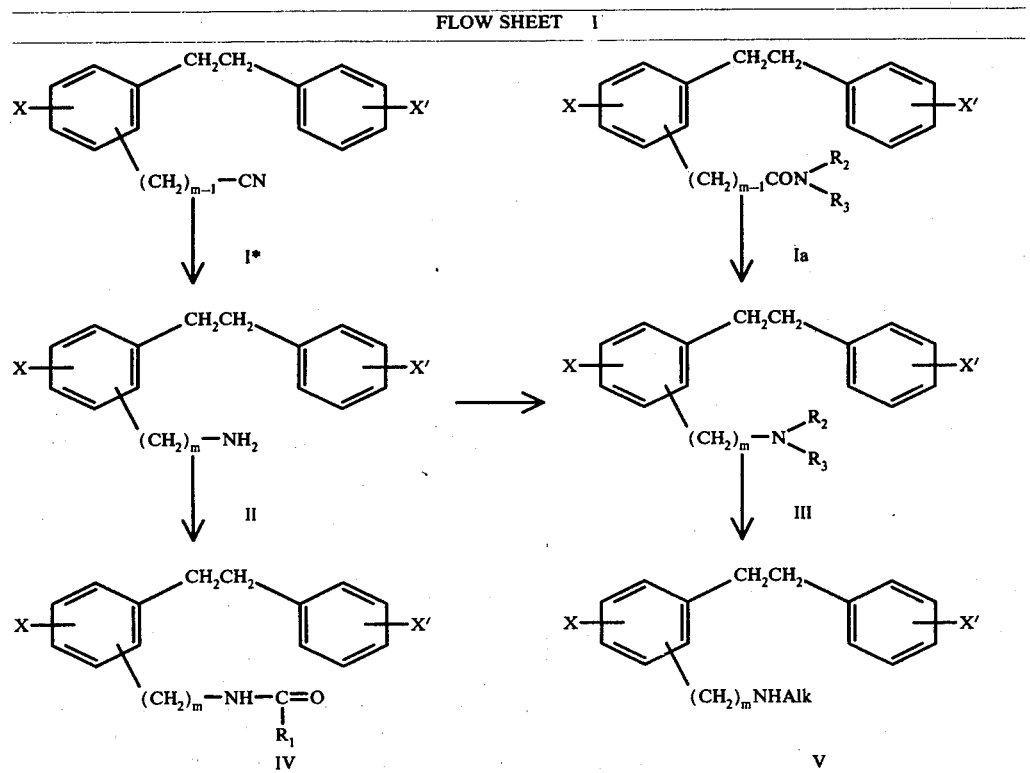

FLOW SHEET 1

*This step may include a homologation procedure involving conversion of the cyano substituent through the conventional sequence of hydrolysis to the corresponding carboxyl derivative, lithium aluminum hydride reduction to CH₂OH, halogenation of CH₂Br and treatment with cyanide ion to the next higher homolog.

wherein
- R₁ is hydrogen or loweralkyl (preferably of from 1–5 carbon atoms);
- R₂ and R₃ can be similar or dissimilar and are either hydrogen, alkyl (preferably of from 1–6 carbon atoms), aralkyl (preferably benzyl or phenethyl), alkenyl, alkynyl, and can be joined together or with one of methylene carbons bridging the amine substituent and the phenyl ring through an atom of nitrogen, oxygen or sulfur to form a heterocyclic ring of from 5–6 atoms (such as imidazolinyl, piperidyl, pyrrolidinyl, morpholinyl, thiomorpholinyl or loweralkyl piperazinyl;
- X and X' are selected from the group consisting of hydrogen, halogen (chlorine or fluorine), alkyl (preferably of from 1–6 carbon atoms), alkoxy (perferably of from 1–5 carbon atoms), perfluoroalkyl (e.g., trifluoromethyl), alkylmercapto (preferably of from 1–6 carbon atoms), alkylsulfonyl (preferably of from 1–6 carbon atoms), and dialkylsulfamoyl (preferably of from 2–8 carbon atoms);
- m is an integer selected from the group consisting of 1–4 inclusive; and
- Alk is alkyl (preferably loweralkyl of from 1–6 carbon atoms).

In accordance with the process of my invention, a substituted or unsubstituted benzonitrile or the correspondingly substituted amide I*a* having a phenethyl substituent is reduced with an alkali metal hydride to form the corresponding benzylamine, e.g., 2-phenethyl benzylamine, 2-phenethyl phenethylamine, 2-(4-bromophenethyl)-benzyl-amine, 2-(4-bromophenethyl)-phenethylamine. The reduction is preferably effected by contacting the nitrile Compound I or the amide I*a* in the presence of a suitable inert organic solvent, such as tetrahydrofuran, ether or other solvents conventionally employed with lithium aluminum hydride. Preferably, this reduction is carried out in the presence of aluminum chloride and an ether compatible with aluminum chloride as a solvent. The temperature at which the reduction is carried out is not critical but it is preferred to employ ambient temperatures and a range of from 0°–50° C. is satisfactory. The resulting benzylamine compound is readily recovered employing conventional techniques.

In preparing higher homologs of the benzylamine compound, the intermediate substituted benzonitrile (I) or compound convertible thereto is converted using conventional reaction methods to produce the desired homologous compound. Thus, the intermediate benzonitrile (I) is hydrolyzed to the corresponding benzoic acid. The thus-obtained acid or ester is then reduced using lithium aluminum hydride to produce the corresponding benzyl alcohol which is recovered in accordance with conventional procedures and treated with a hydrogen halide such as aqueous hydrogen bromide to produce the corresponding benzyl halide, i.e., a benzyl halide of the formula:

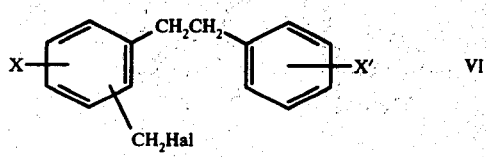

The thus-obtained product is purified using conventional techniques and subjected to treatment with potassium cyanide thereby completing the conversion of the intermediate benzonitrile (I) to the next higher homolog, the phenethylphenylacetonitrile.

The corresponding N-(phenethylbenzyl)-formamide (IV) or higher homolog thereof in which R₁ is hydrogen is prepared by formylation of the benzylamine compound (II) employing conventional conditions and reagents such as formic acid or esters thereof for this purpose. The resulting formamide derivative can be recovered in conventional manner. The N,N-dimethylamine (III), wherein R₂ and R₃ each represent methyl, is readily prepared by the treatment of the primary amine compound (II) with formaldehyde and formic acid in accordance with the known Eschweiler-Clarke modification of the Leuckart Reaction. Recovery of the N,N-dimethylamine is accomplished in conventional manner. The N-methylbenzylamine, represented by (V) wherein Alk is methyl, may be prepared by either reduction of the corresponding N-(phenethenyl or phenethynyl-benzyl)-formamide (IV) or by monodealkylation of the corresponding N,N-dimethylamine (III) wherein R₂ and R₃ each represent methyl. Reduction of the formamidomethyl derivative is effected utilizing lithium aluminum hydride under the conditions set forth above for carrying out the reduction of the corresponding benzonitrile (I). Similarly, dealkylation of the N,N-dimethylamine (III) can be effected in known manner such as by treatment with cyanogen bromide followed by hydrolysis of the intermediate cyanamide or by treatment with a haloformate followed by hydrolysis of the resulting urethane intermediate. In each instance, the desired compound can be recovered employing conventional techniques.

The N-loweralkylamines and the N,N-diloweralkylamines corresponding to compounds (V) and (III), respectively, are likewise prepared from the corresponding primary amine (II) by analogous reactions. Thus, the primary amine (II) is treated with a lower aliphatic acid halide or anhydride of from 2–5 carbon atoms, e.g., acetyl chloride, acetic anhydride, propionyl chloride, butyryl chloride or valeryl chloride to produce the N-alkanoyl amide corresponding to (IV) as, for example, the N-acetyl, N-propionyl, N-butyryl or N-valeryl amide. The thus-obtained amide is reduced to the corresponding N-loweralkyl benzylamine compound (V) by reduction in the manner described for the corresponding benzonitrile compound (I), i.e., by reduction with lithium aluminum hydride. The secondary amine compounds (V) produced in this manner are the N-loweralkyl derivatives of 2-phenethylbenzylamines as, for example, the N-ethyl, N-propyl, N-butyl and the N-amyl derivatives. The corresponding tertiary amines (III), the N,N-diloweralkyl derivatives, are prepared from the secondary amines by repeating the process employed in the preparation of the secondary amines. Thus, the amides of the secondary amines are prepared and reduced with lithium aluminum hydride to produce the corresponding tertiary amines as, for example, the corresponding N,N-diethyl, N-ethyl-N-methyl, N,N-dipropyl, N,N-dibutyl and the N,N-diamyl derivatives of substituted and unsubstituted phenethyl benzylamine.

In accordance with an alternative process for the preparation of the compounds of Formula (III), wherein

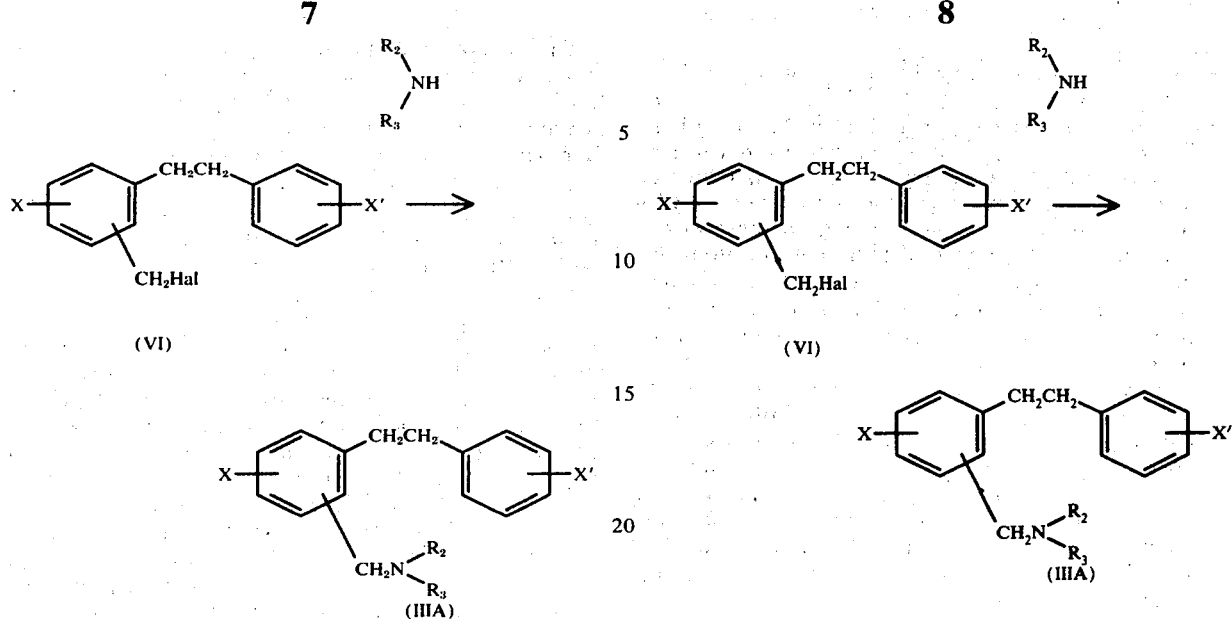

represents 1-pyrrolidinyl, 1-piperidyl, 4-morpholinyl, 4-thiomorpholinyl or 1-loweralkyl-4-piperazinyl, the primary amine (IV) is condensed with an $\alpha,\omega$-dihalo compound such as tetramethylene bromide, pentamethylene bromide, $\beta,\beta'$-dichlorodiethyl ether, $\beta,\beta'$-dichlorodiethyl sulfide, or an N-alkyl-$\beta,\beta'$-dichlorodiethyl amine.

In accordance with a further alternative process for the preparation of the primary, secondary, and tertiary benzylamine products of my invention, a phenethyl benzyl halide of Formula (VI) hereinabove is converted by reaction with ammonia or an amine to produce the corresponding primary, secondary or tertiary amine (IIIA) as indicated below:

wherein Hal, $R_2$, $R_3$, X and X' have the significance previously indicated. In this manner, there is produced in addition to the N-alkyl and N,N-dialkyl derivatives of the substituted and unsubstituted phenethyl benzylamines or higher homologs thereof enumerated hereinabove, the corresponding compounds in which the amine nitrogen forms a part of a heterocyclic ring such as a piperidyl, pyrrolidinyl, morpholinyl, thiomorpholinyl or 1-loweralkyl-4-piperazinyl ring.

The starting compounds of the process of my invention, that is, the arylalkylphenylnitrile and the arylalkylarylamide containing X and x' substituents in the aromatic rings, are either known compounds or may be prepared from the corresponding halo substituted compounds by replacement of the halogen with cyanide through reaction with cuprous cyanide in pyridine. Other similarly substituted compounds may be prepared in accordance with the following flow sheet:

FLOW SHEET II

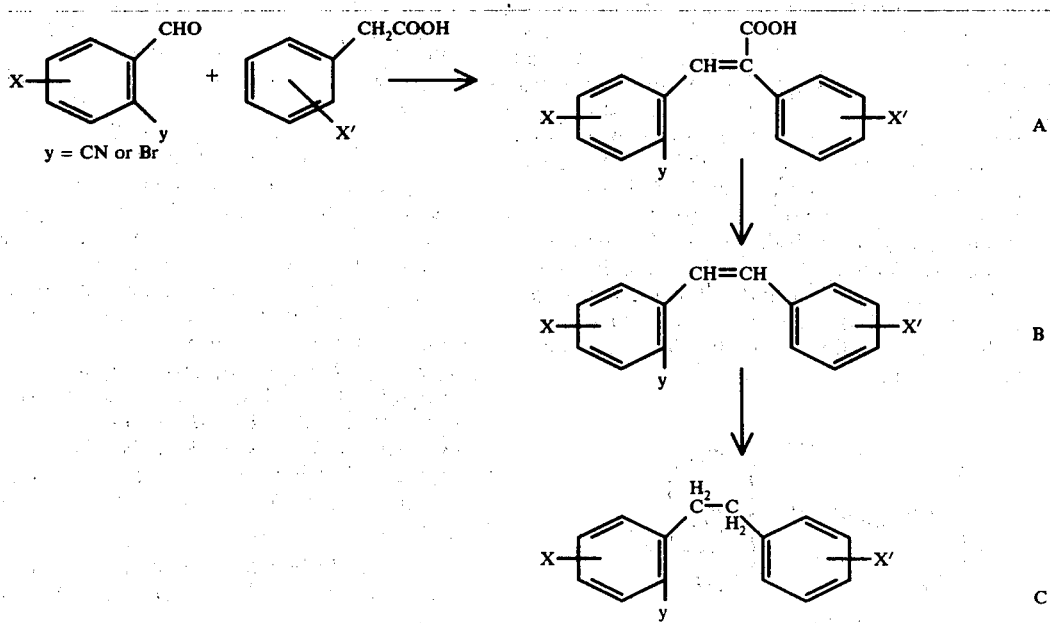

In this instance, a known cyano or bromo substituted benzaldehyde is condensed with a phenyl acetic acid to produce, as a first intermediate compound A, the appropriately substituted phenyl cinnamic acid. This, in turn, is converted to the desired stilbene intermediate by decarboxylation. The stilbene compound in the trans form is then catalytically hydrogenated to produce compound C, an ethane derivative having one aryl substituent attached to each ethane carbon. At any stage of the above-described process, the intermediates used in the preparation of the starting material wherein y is bromo can be converted to the corresponding compound wherein y is cyano by treatment with cuprous cyanide.

EXAMPLE 1

2-(4-Bromophenethyl-N-methylbenzylamine

A. 2-(4-Bromophenethyl)-N-methylbenzamide 2-(4-Bromophenethyl)-benzoic acid, 15 g. (0.049 mole), together with 30 ml. of thionyl chloride and 250 ml. of dry benzene is stirred and heated to refluxing for about 18 hours. Solvent and excess thionyl chloride are evaporated under reduced pressure and the residue is freed from the last traces of thionyl chloride by the twice-repeated addition of dry benzene and evaporation under reduced pressure. The residual oily acid chloride is dissolved in 50 ml. of acetone and the solution added dropwise with stirring to 65 ml. of 40% aqueous methylamine — 25 ml. of water. White precipitate separates but redissolves when the mixture is heated to refluxing for 30 min. On cooling, the product crystallizes and is collected and washed with water; m.p. 138°–141° C. Two recrystallizations from methanol-acetone-ether afford a purified sample, m.p. 142°–143° C.

Anal. Calc'd. for $C_{16}H_{16}BrNO$: C, 60.39; H, 5.07; N, 4.40.

Found: C, 60.51; H, 4.74; N, 4.37.

B. 2-(4-Bromophenethyl)-N-methylbenzylamine

Lithium aluminum hydride, 1.52 g. (0.04 mole), is weighed under nitrogen, transferred to a dry, nitrogen-flushed reaction flask, and suspended in 25 ml. of absolute ether. A solution of 5.34 g. (0.04 mole) of aluminum chloride in 60 ml. of absolute ether is added dropwise. The mixture, containing a white precipitate, is stirred at room temperature for several minutes, then a solution of 6.36 g. (0.02 mole) of 2-(4-bromophenethyl)-N-methylbenzamide in 1.5 l. of absolute ether is added dropwise. The mixture is stirred at reflux for about 18 hours. After cooling, hydrolysis is effected by the dropwise addition of 40 ml. of water. After decantation of the ethereal layer and washing of the gelatinous precipitate with two portions of boiling ether, the precipitate is suspended in 40 ml. of 40% aqueous sodium hydroxide and 160 ml. of water. The mixture is extracted repeatedly with benzene-ether (1:1). Evaporation of solvents under reduced pressure from the washed and dried organic extract leaves the product as the residual oil. The base is converted to the hydrochloride salt by treating a solution in ethanol with a slight excess of ethanolic hydrogen chloride. Dilution with ether precipitates the hydrochloride, m.p. 200°–202° C. Recrystallization from absolute methanol-absolute ether gives an analytical sample, m.p. 199°–200° C.

Anal. Calc'd. for $C_{16}H_{18}BrN.HCl$: C, 56.41; H, 5.62; N, 4.11.

Found: C, 56.71; H, 5.42; N, 4.08.

The base may be converted to the (−) tartrate salt by treating an ethereal solution with a slight excess of (−) tartaric acid in absolute ethanol. The (−) tartrate precipitates, m.p. 150.5°–151.5° C. Repeated recrystallizations from absolute ethanol-absolute ether give purified material, m.p. 151.5°–152.5° C.

Anal. Calc'd. for $C_{16}H_{18}BrN.C_4H_6O_6$: C, 52.87; H, 5.32; Br, 17.59.

Found: C, 52.39; H, 5.18; Br, 17.29.

EXAMPLE 2

N-Methyl-2-phenethylbenzylamine

A solution of 2.0 g. (0.00657 mole) of 2-(4-bromophenethyl)-N-methylbenzylamine hydrochloride in 200 ml. of absolute ethanol — 1 ml. of triethylamine is shaken with hydrogen at atmospheric pressure and 25° C. over 400 mg. of 10% palladium on carbon until hydrogen uptake ceases. The catalyst is removed by filtration, the filtrate evaporated to dryness under reduced pressure, and the residue partitioned between aqueous sodium hydroxide and 1:1 ether-benzene. Evaporation of solvents from the washed and dried organic extract leaves the product as the residual oil. The oily base is converted to the hydrochloride salt by treating a solution in absolute ethanol with a slight excess of ethanolic hydrogen chloride. Dilution with absolute ether precipitates the hydrochloride as white crystals, m.p. 204°–206° C. After repeated recrystallizations from absolute ethanol-absolute ether, an analytical sample melts at 205°–206° C.

Anal. Calc'd. for $C_{16}H_{19}N.HCl$: C, 73.41; H, 7.70; N, 5.35.

Found: C, 73.18; H, 7.44; N, 5.41.

EXAMPLE 3

2-(4-Bromophenethyl)-benzylamine

A. 2-(4-Bromophenethyl)-benzamide

By following essentially the same procedures described in Example 1A, 2-(4-bromophenethyl)-benzamide is obtained from 2-(4-bromophenethyl)-benzoic acid and ammonia. The white crystalline product, m.p. 141°–142° C., is recrystallized repeatedly from ethyl acetate-hexane to yield purified material, m.p. 143°–144° C.

Anal. Calc'd. for $C_{15}H_{14}BrNO$: C, 59.23; H, 4.64; Br, 26.27.

Found: C, 59.33; H, 4.55; Br, 26.64.

B. 2-(4-Bromophenethyl)-benzylamine

By following essentially the same procedures described in Example 1B, 2-(4-bromophenethyl)-benzamide is reduced with lithium aluminum hydride to 2-(4-bromophenethyl)-benzylamine. The product, a light yellow oil, is converted to the hydrochloride salt by treating a solution in absolute ethanol with a slight excess of ethanolic hydrogen chloride. Dilution with absolute ether precipitates the hydrochloride in white crystals, m.p. 189°–190° C. Repeated recrystallizations from absolute ethanol-absolute ether afford an analytical sample, m.p. 194.5°–195.5° C.

Anal. Calc'd. for $C_{15}H_{16}BrN.HCl$: C, 55.15; H, 5.25; Br, 24.46.

Found: C, 54.97; H, 5.13; Br, 24.59.

EXAMPLE 4

2-(4-Bromophenethyl)-N,N-dimethylbenzylamine

A solution of 3.2 g. (0.011 mole) of 2-(4-bromophenethyl)-benzylamine in 9 ml. of 88% formic acid is treated with 2.4 g. (0.03 mole) of 37% formaldehyde and the mixture is heated on the steam-bath for about 18 hours. After the addition of 2 ml. of concentrated hydrochloric acid, the solution is evaporated to dryness under reduced pressure. The residual syrup is dissolved in 30 ml. of water and the cooled solution is rendered strongly alkaline with 40% aqueous sodium hydroxide. The base is extracted into benzene. Evaporation of the washed and dried benzene extract under reduced pressure leaves the product as the residual oil. The base is converted to the hydrochloride salt by treating a filtered solution in absolute ether with a slight excess of ethanolic hydrogen chloride. The hydrochloride pecipitates in white crystals, m.p. 168°–169° C. Repeated recrystallizations from absolute ethanol-absolute ether and from isopropyl alcohol-absolute ether yield purified material, m.p. 173.5°–174.5° C.

Anal. Calc'd. for $C_{17}H_{20}BrN \cdot HCl$: C, 57.56; H, 5.97; Br, 22.53.

Found: C, 57.35; H, 5.87; Br, 22.55.

EXAMPLE 5

2-(4-Bromophenethyl)-phenethylamine

A. Ethyl 2-(4-bromophenethyl)-benzoate

A solution of 40 g. (0.131 mole) of 2-(4-bromophenethyl)-benzoic acid in 250 ml. of absolute ethanol is stirred and heated to refluxing while hydrogen chloride is introduced into the solution for 2 hours. After standing at room temperature for 2½ days, the mixture again is stirred at reflux for 12 hours and, during this period, hydrogen chloride is passed into the solution for 1 hour. The two-phase mixture is evaporated to dryness under reduced pressure and the residue partitioned between benzene and water. The combined benzene layers are extracted with 5% aqueous sodium hydroxide and then washed thoroughly with water and dried over anhydrous sodium sulfate. Evaporation of the solvent and distillation of the residue in vacuo gives the product as the oily distillate, b.p. 142°/0.2 mm.

Anal. Calc'd. for $C_{17}H_{17}BrO_2$: C, 61.27; H, 5.14; Br, 23.98.

Found: C, 61.12; H, 4.89; Br, 23.60.

B. 2-(4-Bromophenethyl)-benzyl alcohol

Lithium aluminum hydride, 3.8 g. (0.1 mole), is wegihed under nitrogen, transferred to a dry, nitrogen-flushed reaction flask, and suspended in 300 ml. of absolute ether. The mixture is stirred at reflux for 30 minutes and then, after cooling to room temperature, a solution of 36.16 g. (0.108 mole) of ethyl 2-(4-bromophenethyl)-benzoate in 100 ml. of absolute ether is added dropwise. The mixture is stirred at room temperature overnight. The excess lithium aluminum hydride is decomposed by the addition of 5 ml. of ethyl acetate and the mixture then is hydrolyzed by the addition of 30 ml. of saturated ammonium chloride solution. The ethereal layer is separated and the aqueous layer re-extracted with ether. Evaporation of the combined, washed, and dried ethereal extracts under reduced pressure leaves the product as the residual solid, m.p. 72°–75.5° C. Recrystallization from hexane-cyclohexane affords purified material, m.p. 74°–75.5° C. A sample for analysis melts at 75°–76.5° C. after recrystallization from hexane.

Anal. Calc'd. for $C_{15}H_{15}BrO$: C, 61.87; H, 5.19; Br, 27.44.

Found: C, 62.13; H, 5.00; Br, 27.64.

C. 2-(4-Bromophenethyl)-benzyl bromide

A suspension of 28.5 g. (0.098 mole) of 2-(4-bromophenethyl)-benzyl alcohol in 150 ml. of 48% hydrobromic acid is stirred at reflux for 3 hours. The cooled two-phase mixture is extracted with benzene. Evaporation of the washed and dried benzene extract under reduced pressure leaves the product as the residual solid, m.p. 63°–75° C. Recrystallization from hexane affords purified material, m.p. 76°–77.5° C. A sample for analysis melts at 76.5°–78° C. after further recrystallization from hexane.

Anal. Calc'd. for $C_{15}H_{14}Br_2$: C, 50.88; H, 3.98; Br, 45.14.

Found: C, 51.03; H, 3.78; Br, 45.21.

D. 2-(4-Bromophenethyl)-phenylacetonitrile 2-(4-Bromophenethyl)-benzyl bromide, 27.0 g. (0.0764 mole) and 6.2 g. (0.0954 mole) of potassium cyanide are suspended in 180 ml. of 95% ethanol and the mixture is stirred at reflux for 2 hours. Ethanol, 70 ml. of 95%, is added and stirring at reflux is continued for 2 hours. The precipitate is removed by filtration and the ethanolic filtrate evaporated under reduced pressure. The residual brown oil is dissolved in benzene and the solution is washed thoroughly with water and dried over anhydrous sodium sulfate. Evaporation of the benzene under reduced pressure leaves the product as the residual dark yellow oil that slowly solidifies to an oily solid. Recrystallization from cyclohexane-petroleum ether gives purified material, m.p. 59°–60.5° C. Vapor phase chromatography indicates a purity of approximately 99%.

E. 2-(4-Bromophenethyl)-phenethylamine

Lithium aluminum hydride, 0.61 g. (0.016 mole), is weighed under nitrogen, transferred to a dry, nitrogen-flushed reaction flask and suspended in 50 ml. of absolute ether. The mixture is stirred at reflux for 30 minutes, then cooled to room temperature and a solution of 2.4 g. (0.008 mole) of 2-(4-bromophenethyl)-phenylacetonitrile in 30 ml. of absolute ether is added dropwise. After 16 hours at reflux, the cooled mixture is hydrolyzed by the successive dropwise addition of 0.7 ml. of water, 0.7 ml. of 20% aqueous sodium hydroxide, and 1.5 ml. of water. The ethereal layer is separated and stirred with 18 ml. of 3N hydrochloric acid. The hydrochloride salt of the product separates, m.p. 148°–153° C. (cloudy melt). Repeated recrystallizations from absolute ethanol-ether and from water yield purified material, m.p. 148°–150° C. (cloudy melt). The hydrochloride is converted to the base by rendering an aqueous solution strongly alkaline. The oily base is extracted into benzene. Evaporation of the washed and dried benzene extract under reduced pressure leaves the product as the residual oil. The base may be converted to the hydrogen maleate salt by treating a solution in methanol with a slight excess of maleic acid. Dilution with absolute ether precipitates the hydrogen maleate in white crystals, m.p. 158°–160° C.

Anal. Calc'd. for $C_{16}H_{18}BrN.C_4H_4O_4$: C, 57.15; H, 5.28; Br, 19.01.
Found: C, 57.49; H, 5.31; Br, 18.93.

EXAMPLE 6

2-(4-Bromophenethyl)-N-methylphenethylamine

A. N-[2-(4-Bromophenethyl)-phenethyl]-formamide

A solution of 0.60 g. (0.00197 mole) of 2-(4-bromophenethyl)-phenethylamine in 20 ml. of ethyl formate is heated to refluxing for about 19 hours. The solution is evaporated to dryness under reduced pressure and the residue dissolved in dry benzene. Evaporation of the solvent under reduced pressure leaves the product as the residual yellow oil.

B. 2-(4-Bromophenethyl)-N-methylphenethylamine

By following essentially the same procedures described in Example 5E, N-[2-(4-bromophenethyl)-phenethyl]-formamide is reduced to 2-(4-bromophenethyl)-N-methylphenethylamine. The product is obtained as an oil that may be converted to the hydrogen oxalate salt by treating a methanolic solution with a slight excess of oxalic acid. The hydrogen oxalate separates in white crystals, m.p. 228°–230° C. Repeated recrystallizations from methanol afford a sample for analysis, m.p. 230.5°–231.5° C.

Anal. Calc'd. for $C_{17}H_{20}BrN.C_2H_2O_4$: C, 55.89; H, 5.43; Br, 19.57.
Found: C, 56.10; H, 5.33; Br, 19.28.

EXAMPLE 7

PREVENTION OR MODIFICATION OF VENTRICULAR ARRHYTHMIA

Beagle dogs of either sex and weighing from 6–10 kg. are anesthetized by the administration of vinbarbital employing a dose of 50 mg./kg. of body weight and the mean arterial pressure and the electrocardiogram (Lead II) are recorded. The animals are artificially respired and the thorax opened at the fourth or fifth interspace. The pericardium is opened and a portion of the anterior descending coronary artery just distal to the origin is freed from the surrounding tissue. Mecamylamine is administered to alow the heart rate and 10 minutes later the compound to be tested for antiarrhythmic effect is administered intravenously. Ten minutes after administration of the test compound, 0.0035 ml./kg. of tetrafluorohexachlorobutane (TFHCB), a sclerosing agent which produces myocardial infarction and arrhythmia in dogs (Ascanio et al., J. Am. Physiol. 209: 1081–1088 (1965)) is injected into the coronary artery. In control animals, this dose of TFHCB produces a ventricular arrhythmia in 100% of the animals tested and death in 33% of the animals tested as a result of ventricular fibrillation.

Following injection of the sclerosing agent, an electrocardiogram is recorded at two-minute intervals for one hour and the average number of electrical (ECG) complexes per minute and the percent normal complexes calculated. The data obtained with different doses of the test compounds is plotted and the dose estimated to protect the animals is estimated graphically ($ED_{80}$mg./kg.). This figure indicates that 80% of all the electrical (ECG) complexes are normal. The compounds of my invention, including 2-(4-bromophenethyl)-N-methylbenzylamine and 2-(4-bromophenethyl)-N,N-dimethylbenzylamine are active as antiarrhythmic agents when tested in the above animal test procedure.

EXAMPLE 8

CAPSULES

Capsules for oral administration are prepared by dispersing the active ingredient in lactose and magnesium stearate and encapsulating the mixture in standard soft gelatin capsules so that each capsule will have the following composition:

|  | Per Capsule |
| --- | --- |
| N-methyl-2-phenethylbenzylamine hydrochloride | 5 mg. |
| Lactose | 430 mg. |
| Magnesium Stearate | 5 mg. |

EXAMPLE 9

PARENTERAL SOLUTION

A solution suitable for administration for injection is prepared by mixing the active ingredient, dextrose, methylparaben, propylparaben and distilled water, so that each one will have the following composition, and sterilized:

|  | Per ml. |
| --- | --- |
| 2-(4-bromophenethyl)-benzylamine hydrochloride | 5.0 mg. |
| Dextrose | 44.0 mg. |
| Methylparaben | 1.5 mg. |
| Propylparaben | 0.2 mg. |
| Water for injection | q.s. |

EXAMPLE 10

TABLETS

Tablets for oral administration are prepared by mixing the active ingredient with appropriate amounts of excipients and binding agents, formed into tablets by a conventional tableting machine, and coated so that each tablet will have the following composition:

|  | Per Tablet |
| --- | --- |
| 2-(4-bromophenethyl)-benzylamine hydrochloride | 10.0 mg. |
| Cellulose filter aid | 11.0 mg. |
| Lactose | 9.0 mg. |
| Calcium phosphate dibasic | 143.0 mg. |
| Guar gum | 6.1 mg. |
| Corn starch | 4.0 mg. |
| Magnesium stearate | 0.9 mg. |
| Opaque yellow film coating | 3.0 mg. |

The preceding three examples, Examples 8, 9 and 10, are repeated, and compositions for the treatment or prevention of arrhythmia are prepared by substituting any of the compounds specifically illustrated above in place of the phenethylbenzylamine as one of the active compounds useful in my invention.

What is claimed is:

1. A method for treating cardiac arrhythmia in animals which comprises administering to an afflicted animal an antiarrhythmic dose of an active compound having the formula

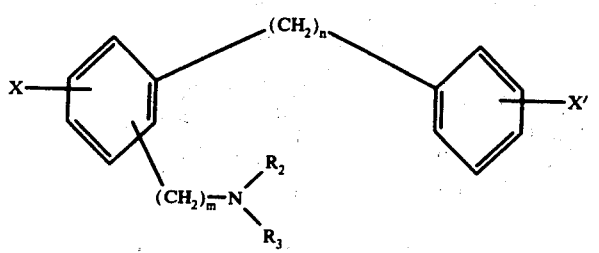

or a pharmaceutically acceptable salt thereof, wherein
X and X' are selected from the group consisting of hydrogen, halogen, alkyl of from 1–6 carbon atoms, alkoxy of from 1–5 carbon atoms, perfluoroalkyl, alkylmercapto of from 1–6 carbon atoms, alkylsulfonyl of from 1–6 carbon atoms, and dialkylsulfamoyl of from 2–8 carbon atoms;

$R_2$ and $R_3$ are each $-CH_2-CH_2-$ and are taken together with said

atom through an atom of oxygen or sulfur to form the morpholinyl or thiomorpholinyl group;
$m$ is an integer selected from the group consisting of 1–4 inclusive; and
$n$ is an integer selected from the group consisting of 1–3 inclusive.

2. The method of claim 1 wherein $R_2$ and $R_3$ are taken with said

atom through an oxygen atom to form the morpholino group.

* * * * *